(12) United States Patent
Knaack

(10) Patent No.: US 6,599,516 B1
(45) Date of Patent: Jul. 29, 2003

(54) MALLEABLE IMPLANT CONTAINING SOLID ELEMENT THAT RESORBS OR FRACTURES TO PROVIDE ACCESS CHANNELS

(75) Inventor: David Knaack, Somerville, MA (US)

(73) Assignee: Etex Corporation, Cambridge, MA (US)

( * ) Notice: Subject to any disclaimer, the term of this patent is extended or adjusted under 35 U.S.C. 154(b) by 0 days.

(21) Appl. No.: 09/661,828

(22) Filed: Sep. 14, 2000

(51) Int. Cl.$^7$ .......................... A61F 2/00; C12N 11/14; C12N 11/02; C12N 5/06; C12N 5/08
(52) U.S. Cl. ................. 424/423; 424/93.7; 435/176; 435/177; 435/395
(58) Field of Search ................. 424/93.7, 423, 424/424; 435/176, 177, 180, 395

(56) References Cited

U.S. PATENT DOCUMENTS

| | | | |
|---|---|---|---|
| 5,336,264 A | 8/1994 | Constanz et al. | 623/16 |
| 5,492,697 A | 2/1996 | Boyan et al. | 424/422 |
| 5,525,148 A | 6/1996 | Chow et al. | 106/35 |
| 5,605,713 A | 2/1997 | Boltong | 427/2.1 |
| 5,683,461 A | * 11/1997 | Lee et al. | 623/16 |
| 5,717,006 A | 2/1998 | Daculsi et al. | 523/115 |
| 5,803,963 A | 9/1998 | Dry | 106/677 |
| 6,001,394 A | 12/1999 | Daculsi et al. | 424/489 |
| 6,027,742 A | 2/2000 | Lee et al. | 424/422 |
| 6,027,744 A | 2/2000 | Vacanti et al. | 424/426 |
| 6,132,463 A | * 10/2000 | Lee et al. | 623/16 |
| 6,309,635 B1 | * 10/2001 | Ingber et al. | 424/93.7 |

FOREIGN PATENT DOCUMENTS

WO  WO 99/16479  4/1999

OTHER PUBLICATIONS

Mundy, "Bone Remodeling and its Disorders," Cellular Mechanisms of Bone Resorption, Martin Dunitz Ltd 1999.
Langstaff, "Calcium Phosphate Ceramics Capable of Supporting Osteoclastic Resorption," (seminar) Oct. 20, 1998, University of Guelph.
Raisz, "Mechanisms and Regulation of Bone Resorption by Osteoclastic Cells," Disorders of Bone and Mineral Metabolism, Raven Press, Ltd. 1992.
Robey et al., "The Cellular Biology and Molecular Biochemistry of Bone Formation," Bone Formation Biology and Biochemistry, Raven Press 1992.
Vacanti et al., "Selective Cell Transplantation Using Bioabsorbable Artificial Polymers as Matrices," Selective Cell Transplantation, Journal of Pediatric Surgery, vol. 23, No. 1, 1988.

* cited by examiner

*Primary Examiner*—David M. Naff
(74) *Attorney, Agent, or Firm*—Hale and Dorr LLP

(57) ABSTRACT

A malleable implant for implantation into living tissue is prepared having access means for cells into the interior of the implant. The implant is capable of being deformed under pressure required to insert the implant into an implant site. The access means can be hollow or solid. The solid comprises a material that more rapidly resorbs in vivo than the malleable implant to provide channels, or comprises a mechanically weak material that fractures under force at an implant site to produce channels or cracks. The access means may be inserted in the malleable implant at an implant site. A multilaminar structure may be formed having layers of malleable implant and layers of access means, or the access means may be heterogeneously distributed throughout the malleable implant. A kit can contain a powder such as calcium phosphate for making a paste implant material, and an access means insertable into the paste.

67 Claims, 2 Drawing Sheets

MALLEABLE IMPLANT CONTAINING SOLID ELEMENT THAT RESORBS OR FRACTURES TO PROVIDE ACCESS CHANNELS

BACKGROUND OF THE INVENTION

This invention relates to implant materials having access channels for enhanced cell-mediated resorption of the implant into living tissue. This invention also relates to materials for the cell-mediated remodeling of an implant.

Damage to body tissue often requires the use of an implant material to replace, support or repair the damaged tissue. For example, implants may be used in the repair of bone fractures or periodontal defects, replacement of damaged cartilage and soft tissues such as muscle tissue and collagen.

In the case of fracture, disease or other injury to bone, proper healing and bone remodeling depends on the successful stabilization of the bone site and the ability to induce bone regeneration and repair. In the instances where damage to the bone is large, a bone graft material (implant) may be introduced into the bone site to bridge the gap left by the damaged bone in order to fill open spaces and prevent fibrous ingrowth into the defect, as well as to aid in the stabilization of the fracture. Often times a resorbable bone graft material is selected to serve this function. Both biologically derived materials such as autographs and allografts, as well as synthetic glasses, calcium phosphates and calcium sulfates, are examples of resorbable bone graft materials.

A variety of synthetic bone implants have been shown to be resorbed or partially resorbed by host cells. Cells which are recognized as important in the resorption process include osteoclasts, osteoblasts, macrophages and vascularizing elements. Since these cells necessarily gain access to the implant by way of the surface, specific surface characteristics may significantly affect remodeling and resorption rates. For example, the ratio of implant surface area to implant volume is expected to have significant ramifications on implant resorption and remodeling rates by cells.

A variety of materials have been proposed for use as bone implant materials, including porous metals, biodegradable organic polymers, and ceramic materials. The use of calcium phosphate materials as implants in bone sites is known. Calcium phosphate cements represent biocompatible materials which provide the components necessary for the formation of bone, namely, calcium and phosphate ions, and which may act as a substrate for bone growth, i.e., they are osteoconductive.

Materials for use as implants range from substantially non-resorbable materials, i.e., porous metals, bioglass and corraline, to highly resorbable materials, i.e., selected organic polymers, calcium phosphates, and composites thereof. In most applications, it is desirable to have materials which are highly resorbable, and which can be replaced by living tissue in a short time period. Furthermore, the implant material ideally is capable of being formed into complex shapes that fit the contours of the repair site. An accurately contoured implant will enhance the integration of natural tissue at the site.

Calcium phosphate cements are known, which set rapidly at room and/or body temperature. See, U.S. Pat. Nos. 5,522,893, 5,525,148, RE 33,161 and RE 33,221 to Chow et al, U.S. Pat. No. 5,605,713 to Boltong et al. and U.S. Pat. No. 5,336,264 to Constantz et al. Such cements provide the ability to form complex shapes with intimate host bone contact, however, the osteoconductivity and the remodeling capability of the resulting material may often be less than desired.

Lee et al. in U.S. Pat. Nos. 5,683,461 and 5,783,217 describe a bioresorbable calcium phosphate cement which is an excellent osteoconductive substrate. The calcium phosphate implant is resorbed in as little as 3–12 weeks in small animal models, and bone tissue substantially similar to naturally occurring bone is formed in its place. Even in these calcium phosphate cements, the remodeling capability sometimes is less than ideal, particularly when they are used to produce large volume implants.

Porosigens have been used to increase porosity in materials. Porosigens include additives, usually particulate in nature, which are leached out or dissolved to form pores or voids which increase the porosity of the implant. While porosigens have been associated with increased resorbability, known porosigens do not provide adequate access to the interior of the implant on a scale sufficient to permit cell-mediated resorption or remodeling of the implant.

Chow et al in U.S. Pat. No. 5,525,148 report the use of pore-forming agents to create pores sufficiently large to cause vascularization of tissue which infiltrates the cement once placed in the body. Chow reports the addition of particulate additives such as sugars, sodium bicarbonate or phosphate salts, which are removed by resorption into the body tissue, dissolution in physiological fluids, or heating after the cement has hardened (presumably before implantation). Due to the nature of the particulate additive, the pores are on the micron or submicron scale, i.e., "non-macro" scale, and the internal porosity remaining after the porosigen is removed is random and often non-continuous.

Solid ceramic implants have been prepared in a variety of sizes and shapes.

Johnson et al. in WO 99/16479, entitled "Bone Substitute Materials", describe a hard, open ceramic framework as a bone implant material. The porous structure is obtained by coating an open-celled organic material with a ceramic oxide and then sintering to burn out the open-celled material.

Boyan et al. in U.S. Pat. No. 5,492,687, entitled "Biodegradable Implant for Fracture Nonunions," describe a substitute bone graft material having interconnected pores and canals having the size, shape and spacing corresponding to Haversian canals, i.e., naturally occurring canals of cortical bone which allow vascularization. The implant is formed by casting a polymeric gel into the desired shape, including channels, and drying to form a solid implant.

In the above examples, the implant is a solid structure in which the porous substructure is introduced into the material prior to implant. Such implant structures are not moldable or able to form complex shapes with intimate host bone contact.

There remains a need to provide an implant material and methodology, in which access into the interior of the implant material is provided, while retaining the host-conforming ability of a paste or putty.

Furthermore, there remains a need to increase the rate and level of cellular ingress into the implant so that the remodeling rate and efficiency of implant material is enhanced.

There remains a need for providing greater access to cells of living tissue to the interior of an implant material to increase implant resorption and tissue remodeling.

SUMMARY OF THE INVENTION

The present invention provides means for cellular access into the interior of a malleable implant to optimize cell contact with the implant material. The access means is a macrostructure that provides access to the interior of a soft, conformable implant material, which upon hardening provides a structural access channel for cells to the interior of the implant.

In one aspect, the inventive implant includes a malleable implant material, and a non-particulate access means for providing macroscopic access into the interior of the implant to cells of the living tissue.

In preferred embodiments, the implant has at least one cross-sectional dimension of greater than 3 mm, and preferably at least one cross-sectional dimension of greater than 1 cm.

In other preferred embodiments, the malleable implant material is comprised of a bioresorbable material and a physiologically acceptable fluid. The malleable material is selected from the group consisting of calcium phosphates, collagens, and fibrins. In one embodiment, the malleable implant material is hardenable, or the malleable implant material is an osteoconductive material.

In one embodiment, the calcium phosphate is selected from the group consisting of amorphous calcium phosphate, tricalcium phosphate, hydroxyapatite, calcium deficient hydroxyapatite, poorly crystalline hydroxyapatite (PCHA), calcium deficient hydroxyapatite, dicalcium phosphate dihydrate (DCPD), tetracalcium phosphate, and dahlite ($Ca_5(PO_4,CO_3)_3F$).

In a preferred embodiment, the non-particulate access means is selected from the group consisting of tubes, rods, fibers, sheets, star-shapes, jack-shapes, fibrous mats, and complex structures. The non-particulate access means may be hollow and open at at least one end and contactable with living tissue, and having an inner diameter of a size which permits access by cells of the living tissue. The non-particulate access means may be solid, having at least one end contactable with living tissue, and having an outer diameter of a size which permits access by cells of the living tissue. In one embodiment, the non-particulate access means is non-resorbable, and may be selected from the group consisting of sintered ceramics, poly(methylmethacrylate), and high molecular weight polyethylene. In other embodiments, the non-resorbable non-particulate access means is positioned and arranged so that the macrostructure terminates in the interior of the implant.

In one embodiment, the non-particulate access means is resorbable, and may be selected from the group consisting of poly(lactide), poly(lactide-co-glycolide), gelatins, collagen, alginate, tissue culture medium, calcium phosphates, calcium sulfate, sugars, carbohydrates, and salts. The non-particulate access means includes a material resorbable by dissolution, enzymatic or cellular action to provide cellular access to the interior of the implant, and preferably includes a nutrient of a cell of the living tissue.

In other embodiments, the non-particulate access means includes a polymer capable of acting as a substrate for cell attachment, and further may include a material for promoting cell adhesion.

In preferred embodiments, the non-particulate access means has a dimension greater than 0.5 mm, and preferably a dimension greater than 1 mm, and more preferably greater than 5.0 mm.

In other preferred embodiments, the non-particulate access means is insertable into the malleable implant material at an implant site. In one embodiment, the implant is a multilaminar structure having layers of malleable implant material and non-particulate access means. In other embodiments, the non-particulate access means is heterogeneously distributed throughout the implant.

In other preferred embodiments, the non-particulate access means includes a mechanically weak material susceptible to fracture at an implant site thereby resulting in channels or cracks, and may be selected from the group consisting of hydrogels, oils, lipids, lubricants, sugars and salts.

In one embodiment, the inventive implant further includes additives capable of controlling the resorption rate of the implant material, and may be selected from the group consisting of bone morphogenic protein, OP-1 parathyroid hormone, parathyroid-hormone-related peptide, 1,25-dihydroxyvitamin D, interleukin-1, tumor necrosis factor, thyroid hormones, vitamin A, transforming growth factor/epidermal growth factor, fibroblast growth factor, heparin, bacterial endotoxin, thrombin, bradykinin, prostaglandin $E_2$ and other protanoids, transforming growth factor $\beta$, lymphocyte inhibitory factor/differentiation inducing factor, calcitonin and related peptides, interferon-$\gamma$, glucocortinoids, estrogens and androgens.

In another embodiment, the inventive implant further includes reinforcing additives.

In another aspect of the invention, a kit is provided having a powder for use in preparing a paste, and a macrostructure insertable into a paste, said macrostructure providing access to a cell to the interior of the paste. In preferred embodiments, the powder includes a calcium phosphate. In other preferred embodiments, the kit further includes a mixing pouch, or a physiologically acceptable fluid.

In yet another aspect of the invention, a method of enhancing remodeling at an implant site is provided. The method includes the steps of implanting a malleable implant material at a host site and, before or after the step of implantation, introducing non-particulate access means into the malleable implant material for providing macroscopic access into the interior of the implant material to cells of the host, whereby cells of the host are introduced into the interior of the implant material. In preferred embodiments, the access means are introduced after implantation.

In one embodiment, host cells preferentially act upon the access means to degrade and thereby remove the access means to create a conduit within the implant.

In preferred embodiments, the method includes an implant having at least one cross-sectional dimension of greater than 3 mm, and preferably at least one cross-sectional dimension of greater than 1 cm.

In other preferred embodiments, the method includes a malleable implant material comprised of a bioresorbable material and a physiologically acceptable fluid, and the malleable implant material may be hardenable or it may be an osteoconductive material, such as calcium phosphates, collagens, and fibrins.

In other embodiments, the calcium phosphate is selected from the group consisting of amorphous calcium phosphate, tricalcium phosphate, hydroxyapatite, calcium deficient hydroxyapatite, poorly crystalline hydroxyapatite (PCHA), calcium deficient hydroxyapatite, dicalcium phosphate dihydrate (DCPD), tetracalcium phosphate, and dahlite ($Ca_5(PO_4,CO_3)_3F$).

In yet other embodiments, the method includes non-particulate access means selected from the group consisting of tubes, rods, fibers, sheets, star-shapes, jack-shapes, fibrous mats, and complex structures. It may be hollow and open at at least one end, contactable with living tissue, and having an inner diameter of a size which permits access by cells of the living tissue. It may be solid, having at least one end contactable with living tissue, and having an outer diameter of a size which permits access by cells of the living tissue.

In some embodiments, the method includes non-resorbable, non-particulate access means is non-resorbable, and may be positioned and arranged so that the macrostructure terminates in the interior of the implant.

In other embodiments the method includes resorbable, non-particulate access means and may be selected from the group consisting of poly(lactide), poly(lactide-co-glycolide), gelatins, collagen, alginate, tissue culture medium, calcium phosphates, calcium sulfate, sugars, carbohydrates, and salts. The non-particulate access means is comprised of a material resorbable by dissolution, enzymatic or cellular action to provide access to the interior of the implant. The non-particulate access means is comprised of a nutrient of a cell of the living tissue, or a polymer capable of acting as a substrate for cell attachment. The implant may further include a material for promoting cell adhesion.

In yet other embodiments, the method includes a non-particulate access means having a dimension greater than 0.5 mm, preferably greater than 1 mm, and more preferably greater than 5.0 mm.

In other embodiments, the non-particulate access means is inserted into the malleable implant material at an implant site, or it may be a multilaminar structure having layers of malleable implant material and non-particulate access means, or it may be heterogeneously distributed throughout the implant.

In other embodiments, the method includes a mechanically weak non-particulate access means susceptible to fracture at an implant site and a force is applied to the implant to thereby result in channels or cracks.

In still other embodiments, the implant may further include additives capable of controlling the resorption rate of the implant material, or reinforcing additives.

Definitions

"Access means" is used herein to mean a structural element that is introduced into an implant material to provide cells access to the implant interior. The access means may provide such access either by providing empty conducts, voids or channels through which cells may pass, or by preferential resorbability or dissolution, or by preferential material failure which has the effect of introducing breaks, channels or other access pathways into the implant interior.

"Biocompatible" means that the material does not elicit a substantial detrimental response in the host, such as for example, an immune response or an inflammatory response having a negative effect on the host. A material is considered biocompatible when the host responses are within medically acceptable ranges.

"Bioresorbable" means the ability of a material to be resorbed or remodeled in vivo. The resorption process involves degradation and elimination of the original implant material through the action of body fluids, enzymes or cells. The resorbed materials may be used by the host in the formation of new tissue, or it may be otherwise re-utilized by the host, or it may be excreted.

"Cellular action or process" involves an enzymatic or metabolic process carried out by a cell. The degradation and/or breakdown of the implant material resulting from the cellular process may be the result of enzymatic processes involving enzymes such as phosphatase which hydrolyzes phosphomonoesters (phosphates) or hydrolase which catalyzes the hydrolysis of a variety of bonds, such as esters, glycosides, peptides or by means of cell-mediated acidification as is known to occur during osteoclast resorption of bone.

"Implant interior" is that portion of the implant which is not immediately accessible from the surface, or which is accessible to the surface only through an access channel and is some distance from the surface. Generally, as used herein implant interior refers to a portion of the implant which is, at the time of implantation, more than 5 mm from any surface, more than 2 mm and always 1 mm from the implant outer surface. Determination of distance from surfaces is not measured from any surface defining an access channel.

"Macrostructure" means a structure having dimensions on the order of millimeters or more. The macrostructure preferably has at least one cross-sectional dimension of at least 0.1 mm, and more preferably at least 1.0 mm. The dimension of the structure is selected to accommodate cells, blood vessels (vasculature) and other organelles needed to sustain the living tissue. Osteoclasts, which are a preferred cell for remodeling of bone, typically have diameters on the order of 0.1–0.3 millimeters. Vascularization generally requires even larger access dimensions to accommodate the multitude of capillaries formed in the vascularization process.

"Malleable" means capable of being shaped or deformed under pressure or other force. In the present invention, the pressure is applied in conjunction with introduction or insertion of channel makers into the malleable implant paste, or introduction of the malleable implant material into an implant site.

"Non-particulate" means a material that is not in a powder or a particulate form, that is, the material is not a powder, fragment, granule, grain or particle. However, the material may be comprised of particulate subcomponents which have been combined to form a larger unitary structure, such as can be obtained using powder compaction and powder pressing techniques. The non-particulate member has at least one cross-sectional dimension on the order of at least 0.1 mm, preferably at least 1 mm and more preferably at least 0.5 cm, and can range much higher, e.g. ~5 cm, in some instances.

"Resorption" means the loss of substance (mass) through physiological means, such as those processes involved in loss of dentin and cementum of a tooth or of the alveolar process of the mandible or maxilla. In the present invention, resorption involves the loss of implant mass which has been introduced into the host body through normal physical (e.g., dissolution) or physiological processes. "Cellularly resorbable" means a that a material is resorbable by a process involving a cellular process.

"Remodeling" is related to resorption and is the process of coordinately replacing or transforming the resorbed material into tissue without the formation of significant unwanted voids or detrimental intermediates. An exemplary remodeling is the coordinated resorption of a calcium phosphate bone cement and its replacement with new bone.

BRIEF DESCRIPTION OF THE DRAWING

The invention is described with reference to the following figures, which are for the purposes of illustration only and in no way limiting of the invention and in which.

DETAILED DESCRIPTION OF THE INVENTION

Figure 1:
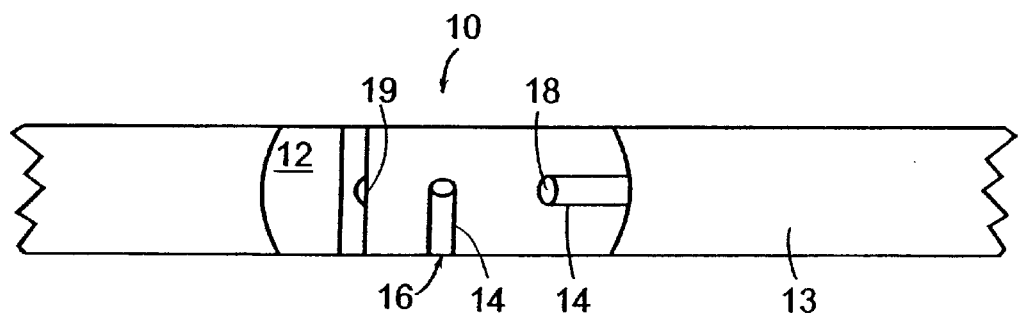
FIG. 1 is a schematic illustration of the implant of the invention including access means.

The present invention provides an implant including a non-particulate access means which increases cell access to the implant interior, e.g., "cellular access," to thereby improve implant resorption and increase tissue remodeling. Use of implants at bony sites is a contemplated application for the implant material of the invention; however, it is recognized that implants also may be used at other sites, including both hard and soft tissues, such as cartilage, muscle, central nervous system, subcutanum and the peritoneum, by way of example only. These and other implant sites are contemplated as applications for the inventive implant. For the purposes of simplicity, the implant of the invention is described for use as a bone implant. It is understood that the implant material may be used in other tissues.

According to the invention, a malleable implant material is provided which is capable of being formed or shaped to provide access means to the implant interior. In preferred embodiments, the malleable implant material is a paste or putty which remains formable for a time sufficient to be deformed or shaped in the manner described herein and which hardens to form a rigid or semi-rigid implant having access means of the invention disposed therein. A malleable implant material provides several unique advantages. Firstly, a malleable material may be used with a wide variety of access means of differing shapes, sizes and functions. Secondly, the ability of a malleable material to harden, i.e., to act as a cement, allows the user to deform the material as needed, including by introducing the malleable implant material into an implant site, and to insert the non-particulate or structural elements used in the formation of the access channels into the malleable implant material, and thereafter, to allow the malleable implant material to harden at the implant site.

Generally speaking, cell-based remodeling occurs from the exterior surface of an implant inward. Thus, cellular remodeling or resorption of the interior portion of the implant generally occurs last in the remodeling process. The present invention allows access to the implant interior early in the process, thereby accelerating the rate of remodeling. As the amount of implant material used in an implant site increases, the relative surface area to volume ratio generally decreases. Since cell contact with osteogenic tissue may often be important in promoting implant remodeling, surface to volume ratio may have a significant effect on cellular interaction with the implant. For a large implant site in which the surface area/volume ratio is relatively small, the number of bone repair cells, e.g., osteoclasts, osteoblasts, macrophages, and vascularization elements gaining access to the implant interior may be insufficient for effective remodeling. The decreased number of osteogenic cells available for bone repair in larger implants slows the absolute rate of resorption of the material and the development of new bone.

The present invention overcomes these and other limitations of the prior art by providing an implant capable of mimicking the natural process of tissue growth. In natural systems, tissue turnover does not necessarily occur from the surface inward, which is the path most readily available for the remodeling of resorption of an implant material. Rather, the tissue turnover generally is initiated throughout the structure. This is possible due to the host's vascular system which provides access to all regions of a tissue. The implant of the present invention uses artificially introduced access channels to provide to living cells of the host a rapid access to the implant interior. By promoting tissue remodeling from within the interior of the implant, the implant can better mimic the natural cell turnover of the living tissue.

The implant material preferably is a paste, putty or material of other formable consistency. By way of example, the paste may be a combination of a powder or a powder mixture with an appropriate amount of liquid to provide the desired paste consistency. Alternatively, the paste may be a gel in which fluid is retained within a network of the biocompatible material. This permits its introduction at the host site in a manner which is easy and which maximizes intimate host-implant contact. As such, the implant is self-forming and can be introduced into a confined space or in a complex shape which would be difficult or impossible using the solid porous structures of the prior art. The paste consistency also allows for the easy introduction of access means into the implant, either prior to or after its introduction to the implant site.

In preferred embodiments, the paste is hardenable. Hardening may occur in a "curing" step, such as for organic polymers, in which completion of the polymerization or crosslinking reaction results in a hardened product. Curing of organic polymers is accomplished with the use of catalysts, crosslinkers, radiation, heat or other means used in the polymerization and/or crosslinking of the paste to form a hardened rigid implant. Hardening may also occur in a "reacting" step in which the combination of the component powders of the paste initiate a reaction leading to a hardened material. Reaction hardening is observed for inorganic cements in a hydraulic process, in which curing occurs with hydration by water, or by reaction of a mixture of cementious materials to form the hardened implant.

In preparing articles of the invention, it is preferable to use a biocompatible material so that there is minimal detrimental immune response on the part of the host to the presence of the implant. Biocompatible materials are well known, and include synthetic organic polymers, such as poly(lactic acid) (PLA), poly(glycolic acid) (PGA), and block copolymers thereof, e.g., PLGA, polyanhydrides, polyorthoesters, naturally occurring polymers, such as collagen, alginate, and the like, inert metals, such as titanium, and the like, as well as ceramic materials, such as calcium sulfate and calcium phosphates, and the like.

In preferred embodiments, the material is bioresorbable. The bioresorbable material is gradually degraded and, the degraded material may either be removed from the site by normal waste removal processes of the host, or it may be used in the remodeling of the implant into living tissue. Many of the above-noted biocompatible materials are also bioresorbable.

Preferred bioresorbable materials include biodegradable organic polymers such as polyorthoesters, polyglycolic acid, polylactic acid, polyanhydrides, and copolymers thereof. Exemplary biodegradable organic polymers include those described in U.S. Pat. No. 5,286,763, which is hereby incorporated by reference.

Other preferred bioresorbable materials include calcium phosphate and calcium sulfate cements. Calcium phosphate cements include calcium- and phosphate-containing components which may be hydrated to form a malleable paste or putty and which subsequently harden by reactions typical to each system. Exemplary calcium phosphates include those found in the following U.S. Pat. Nos.: RE 33,161 and RE 33,221 to Brown et al.; U.S. Pat. Nos. 4,880,610; 5,034,059; 5,047,031; 5,053,212; 5,129,905; and 5,336,264 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat. Nos. 5,717,006 and 6,001,394 to Daculsi et al., U.S. Pat. No. 5,605,713 to Boltong et al., all of which are hereby incorporated by reference.

Exemplary calcium phosphate elements include those prepared from tetracalcium phosphate, tricalcium phosphate or amorphous calcium phosphate hydroxyapatite, calcium deficient hydroxyapatite, poorly crystalline hydroxyapatite (PCHA), calcium deficient hydroxyapatite, dicalcium phosphate dihydrate (DCPD), tetracalcium phosphate, and dahlite ($Ca_5(PO_4,CO_3)_3F$), and a second calcium and/or phosphate source. Exemplary secondary calcium and/or phosphate sources include calcium metaphosphate, dicalcium phosphate dihydrate, heptacalcium decaphosphate, tricalcium phosphates, calcium pyrophosphate dihydrate, stoichiometric hydroxyapatite (HA), poorly crystalline apatitic (PCA) calcium phosphate, calcium pyrophosphate, monetite, octacalcium phosphate, CaO, $CaCO_3$, calcium acetate, $H_3PO_4$, and ACP.

A particularly preferred bioresorbable material is a calcium phosphate cement formed from a powder mixture of amorphous calcium phosphate and dicalcium phosphate dihydrate, as described by Lee et al. in U.S. Pat. Nos. 5,683,461 and 5,783,217 and U.S. Ser. No. 08/729,344, entitled, "Methods And Products Related to The Physical Conversion of Reactive Calcium Phosphate", filed Oct. 16, 1996, which are hereby incorporated in their entirety by reference. The calcium phosphate powder forms a paste with physiological fluids that remains formable for a significant length of time (>30 minutes) at room temperature. This provides the user with sufficient time to introduce the non-particulate access means into the material.

An access means is included in the paste to provide access to the implant interior to cells of the living tissue at the implant site. The particulate additives of the prior art have been found inadequate to allow cellular access to the implant interior. In many instances, the pores formed by prior art porigens are discreet and non interconnected, thus failing to provide adequate access of metabolically important cells far enough into the implant interior. The present invention uses a macrostructure, or non-particulate, element to provide the access means. Access means may be a material which provides a low resistance pathway to cells of the host; it may be a solid or hollow pathway; or it may be a material which promotes pathway formation in either itself or the paste. The access means may be introduced into the paste prior to or after implantation. The access means may be combined with powder precursors to the paste, added to the paste once formed, or inserted into the formable paste once it is applied to the implant site. In preferred embodiments, the access means is introduced into the paste after implantation. In other preferred embodiments, the paste includes only a few access channels which are non-uniformly distributed throughout the paste and which provide access channels on a macro scale e.g., greater than 0.1 mm, greater than 0.5 mm, greater than 1 mm, and preferably greater than 0.5 cm.

The access means are non-particulate structures of a size which permits easy and rapid access to the implant interior by cells of the living tissue. With reference to FIG. 1, a bone implant 10 comprises a formable, biocompatible paste 12, which can be readily formed to conform to the shape of a host site 13, e.g., a non-union bone. The implant further comprises access channels 14, which are macro structures introduced into the paste 12 before or after implantation to provide a low resistance pathway to cells of a living tissue into the interior of the implant. The access channels may an access port 16 which is in contact with the physiological environment of the host tissue and an interior port 18 which is in contact with the implant interior. The interior port may be at a terminal end or located along the surface of the implant at site 19.

FIG. 2 represents some possible architectures for the access means or channels of the invention. The access means may be an elongated structure having one dimension or axis that is significantly greater than the other two. The elongated axis generally is used to connect the implant surface to the implant interior. Dimensions along the elongated axis may be dependent on the implant size, but are typically in the range of 0.2 to 2.0 cm, and preferably in the range of 0.5–1.0 cm. However, in many instances the axis may be larger, extending to 5 cm or more. FIGS. 2A and 2B illustrate two types of extended, elongated structures which may be used, hollow tubes 20 and solid rods 22, respectively. An exemplary version of an elongated solid access means is a resorbable suture embedded within an implant with one or both ends extending to the implant surface.

Figure 2A:
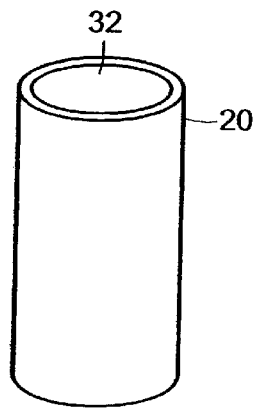
FIGS. 2A–2F are schematic illustrations of various structure and geometries useful as access means of the invention.
Figure 2B:
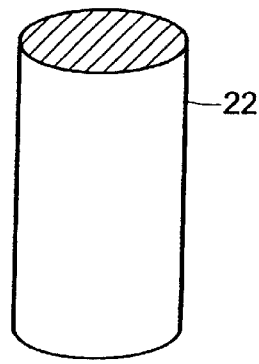
Figure 2C:
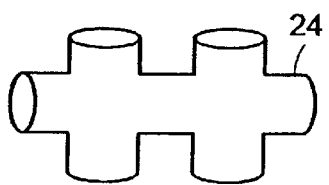
Figure 2D:
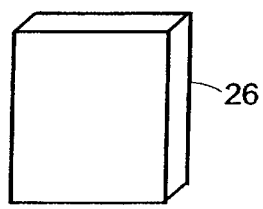
Figure 2E:
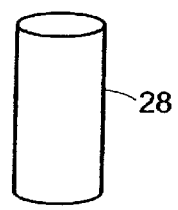
Figure 2F:
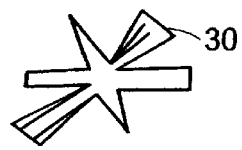

In other embodiments, the access means may be elongated in more than one dimension, i.e., a "two-dimensional" structure. Two-dimensional structures include fabrics or meshes 24 (FIG. 2C), sheets (FIG. 2D) 26 and tapes 28 (FIG. 2E). The two dimensional structures may be cast, molded or woven and may be hollow or solid, as in FIGS. 2A and 2B. It is desired that the structure be semi-rigid or have some physical integrity, i.e., resistance to crushing, which will aid their introduction into the implant. More complex structures are also possible, such as a star-shape structure. Another complex structure is shown in FIG. 2F, which is an exemplary three-dimensional insert 30, reminiscent of a child's toy "jack". In yet another embodiment of the invention, the access means may be a fibrous mat prepared from a plurality of entangled fibers. The small dimension of each individual fiber and the overall volume defined and occupied by the mat make it suitable as a rapidly resorbable access means. Alternative structures in which the number and arrangement of struts are varied will be immediately apparent to one of ordinary skill in the art. In each of these structures, the elements may be hollow or solid.

In one embodiment of the invention, the access means is hollow and open-ended, such as a hollow tube 20, mesh 24, tape 28 or other similar structure, to provide an open pathway for the movement of cells into the implant. The open pathway provided by the access means is preferably greater than 0.1 mm, and more preferably greater than 1 mm. The access channel is positioned in the paste such that an open end 32 of the hollow access means terminates in the interior of the implant. The hollow structure may be resorbable, so that it is rapidly dissolved by physiological fluid, or resorbed by enzymatic action or cellular processes at the implant site to provide channels for cellular interaction. The hollow structure may be porous, either to provide cellular access to the implant interior or to promote rapid resorption by increasing surface area access to physiological environment. Suitable resorbable materials include biodegradable organic polymers, such as PLA, PGA, PLGA, collagen, gelatin, alginate, chitosan, resorbable calcium phosphates, calcium cements, such as calcium sulfate, sugars, such as sucrose, starches, and salts, such as NaCl.

These materials may be used alone or in combination to produce the access means. The access means preferably has a greater resorption rate than the material used for the implant.

In an alternative embodiment of the invention, the hollow access channels are non-resorbable. The access channel is positioned in the paste such that an open end of the hollow access means terminates in the interior of the implant resulting in a permanent feature of the implant. Cells are able to access the implant interior by migrating down the inner passageway of the access channel, which has one or more access ports along its length for cellular access to the implant interior. Such permanent access channels may have the additional advantage of reinforcing or strengthening the implant. Suitable non-resorbable materials include poly (methylmethacrylate) (PMMA), sintered hydroxyapatite, and high molecular weight polyethylene (HMWPE).

In another embodiment of the invention, the access means may be solid, and preferably may be a bioresorbable or a porous solid. By solid it is meant that there is no inner lumen. By porous it is meant that the channel, while lacking an inner lumen, possesses pores on the dimension of cells so that cells may enter and migrate through the access means to approach the implant interior. Pore sizes on the order of 100–300 $\mu$m are contemplated. Suitable resorbable materials include biodegradable organic polymers, such as PLA, PGA, PLGA, collagen, gelatin, alginate, resorbable calcium phosphates, calcium cements, calcium carbonate materials or coral derivatives, such as calcium sulfate, sugars, such as sucrose, starches, and salts, such as NaCl. The access means preferably has a greater resorption rate than the material used for the implant. Other exemplary materials for use as a solid access means includes lipids that are solid at room temperature, but liquid or semi-solid at 37° C.

Preferably the access channel is made of materials which promote cell attachment. In alternative embodiments, the access channel may be coated with a material having high cell attachment. Exemplary materials include Matrigel (Becton Dickinson), RDG peptide ECM component glycoprotein.

In preferred embodiments, the access means is made up of or includes cell growth medium which can support the growth of cells of the living tissue. In other preferred embodiments, the access means includes a source of nourishment for cells of the living tissue. In still other embodiments, growth factors may be included which promote the growth, differentiation and/or proliferation of bone cells. While not being bound by any method or mode of operation, it is presumed that cellular access to the implant interior may be enhanced by providing surfaces or materials for which cells have high affinity for the cells or which serve as a nutrient base for the cells.

The access means described herein may be prepared using conventional methods for preparing articles of a desired shape and size. For example, the means may be prepared in molds, and preferably by compression molding, in which the powders are formed under pressure. Other powder fabrication methods include powder compacting and powder pressing techniques, such as hot isostatic pressing (HIP) and cold isostatic pressing (CIP). They may also be prepared by injection molding or extrusion. Fibrous means may also be prepared using fiber spinning techniques, in which a high concentration solution or melt of the materials is prepared and fibers are drawn from the solution under rapid evaporation or cooling conditions.

A unique feature of this invention is the use of solid or porous access channels on a macroscale, that is greater than 0.1 mm, greater than 0.5 mm, greater than 0.1 mm, greater than 0.5 cm, and greater than 1 cm, and in particular use of access channels that are constructed to take advantage of natural cellular processes for their creation and function. The access channel includes a material which is absorbed more rapidly than the malleable implant or hardened implant material under physiological conditions at the implant site. Once implanted, the access channels are absorbed and/or removed from the implant to leave open channels through which cells of the host may pass. The solid nature of the access means takes advantage of natural cellular processes to create the internal access desired for resorption and tissue remodeling. The access channel may be absorbed in vivo using a variety of methods, including leaching by physiological fluid, cell-mediated digestion, and the like. Preferred materials for use as the access channel include extracelluar matrix materials, such as collagen or fibrin, which are susceptible to in situ proteolysis and degradation.

For example, when the implant material is used as a bone implant, the implant may include a resorbable calcium phosphate-based implant and a second resorbable material as the access means that is rapidly resorbed in vivo, e.g., collagen. The resorption of the rapidly resorbing material making up the access means preferably provides internal access to macrophages, vascularizing elements, osteoclasts and other bone remodeling cells. Osteoclasts are associated with natural bone resorption and it is assumed that the same cellular processes responsible for natural bone remodeling are responsible for the rapid dissolution and resorption of the implant material.

In yet another embodiment of the invention, the access means includes a structure which is mechanically weak, such as hydrogels, oils, lipids, lubricants and loosely pressed powders of sugars or salts. The access means is preferably of a strength less than that of the implant. When the implant is subjected to loads, either during the implantation process or due to the normal activities of the host, the access means fractures and breaks, thereby introducing natural access channels into the implant. The access means of this embodiment is preferably made up of a brittle or friable material such as a highly porous, low compressive strength Ca/P rod or sheet. Alternatively, engineering weaknesses could be designed into the access means. For example, a material which dissolves may be added to the article in the form of a sheet or ribbon. After hardening and dissolution of the channel former, a cleavage plane may be left upon which the implant will fracture.

Figure 3:
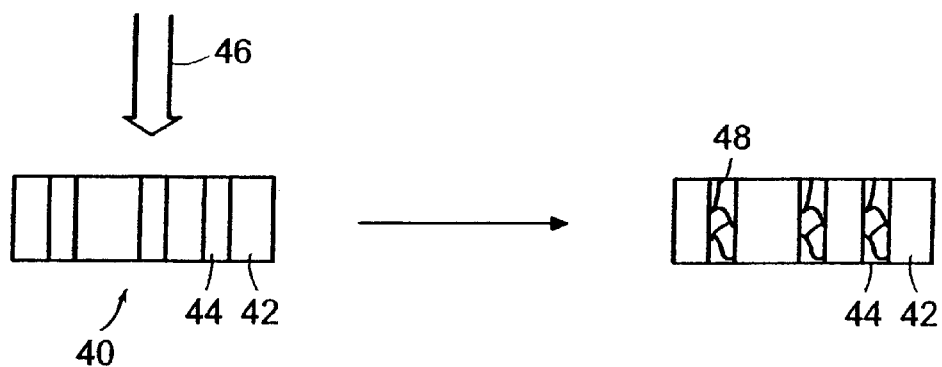
FIG. 3 is an illustration of a mode of access channel introduction into the implant.

The mode of operation of an implant having mechanically weak access means is shown in FIG. 3. A bone implant 40 made up of a formable, biocompatible paste 42 is introduced into a bone site and conformed to the shape of a host site, e.g., a non-union bone. The implant further includes mechanically weak access channels 44. The mechanically weak access channels 44 may be introduced into the paste 42 before or after implantation. After their introduction, a load, indicated by arrow 46 may be applied to the device to cause fracture of the mechanically weak access means. Load may be applied by finger pressure, mechanical means, or may be caused by the normal activities of the host, e.g., sitting, walking, etc. Resultant fractures 48 are shown in FIG. 3B.

The degree of access to the implant interior may be controlled by limiting the number of access channels incorporated into the implant. In cases in which greater resorption is desired, generally, more access channels are incorporated into the paste. Alternatively, a poorly resorbing implant material may require a high level of access channels in order to maintain acceptable levels of resorption. However, an excess of access channels is not desirable, since this may result in an highly porous implant with poor mechanical properties. A very porous material is not suitable for a bone implant, in particular a weight-bearing implant, because the strength and integrity of the implant may be compromised. In an alternative embodiment, the access means may be a non-resorbable tube or hollow rod which provides a means for cell access to the implant interior while strengthening and structurally reinforcing the implant.

The appropriate level of access channels represents a balance between the desired resorption and the structural integrity of the implant. In preferred embodiments, access channel are present at as high a density as is possible without compromise to the required strength of the implant. Depending on the implant site, i.e., whether it is a weight-bearing site, etc., the actual number of access channels used may vary.

Other materials may be included in the implant. For example, in order to optimize tissue remodeling, the implant may be seeded with cells of the living tissue. By way of further example, a bone implant may be seeded with bone-forming cells, such as osteoclasts. Similarly, the implant may be seeded with chondrocytes or other cartilage-forming cells for situations where cartilage formation is desired. The implant may be seeded by contacting the paste with a source of the host's own bone forming cells. Such cells are typically found in bone-associated fluids, including exogenous fluids which have been in contact with bone or bone materials, including the cortical or cancellous bone or marrow. In yet other embodiments, it may be useful to prepare the bone site of implantation by removing a portion of cortical bone. Other steps may be taken to induce bone growth, such as introducing bone forming cells harvested from the host into the implant. Non-autologous bone cells are also within the scope of the invention if the desired amount of bone regeneration may be obtained prior to rejection of the cells by the host. Thus, cells or tissues obtained in cell lines or cell banks may all be useful in certain embodiments.

It is also possible to introduce trophic factors or bone growth-inducing proteins into the implant.

The resorption of the implant may be further modified by inclusion of certain bone resorption regulators into the implant. For example, stimulators may be incorporated to promote or stimulate the resorption of a calcium phosphate paste used as an implant material. Exemplary stimulators include OP-1 parathyroid hormone, parathyroid-hormone-related peptide, 1,25-dihydroxyvitamin D, bone morphogenic protein, interleukin-1, tumor necrosis factor, thyroid hormones, vitamin A, transforming growth factor/epidermal growth factor, fibroblast growth factor, heparin, bacterial endotoxin, thrombin, angiogenic factors such as Veg-F, and bradykinin.

The above-mentioned additives may be included in either the paste of the implant material or the access channel material. In particular, it may be desirable to include bone-forming cells directly in the access channel to further promote cell access to the interior of the implant.

Other supplemental materials may be included in the implant to impart desirable properties to the implant, such as reinforcing agents, lubricants, antibiotics, and the like. Suitable supplemental material for inclusion in the implant are described in WO 98/16268, which is incorporated in its entirety by reference.

The inventive implant may be supplied to the user in a variety of forms, including as a powder or as a powder mixture, which is added to a liquid component to make a paste. The access means may be separately provided for addition to the paste once formed, either before or after introduction of the paste into a host site. Alternatively, the implant may provided as a pre-mixed paste, either with or without a non-aqueous extender of low volatility. It may be supplied with or in instrumentation to introduce the implant into the body, for example, a syringe, percutaneous device, cannula, and the like, which will be apparent to those of ordinary skill in the art. It is contemplated that the, implant may be made available to surgeons, doctors, dentists, and/or veterinarians in a kit containing one or more of the key components of the implant, and including some or all of the components necessary for its administration.

The implant material may be prepared outside the host in a variety of forms and may be introduced into the host at the implant site using methods appropriate to the form of the implant and the nature of the malady. The implant device of the invention having access channels on the macroscopic scale is best suited for situations requiring a large volume of implant material, e.g., on the order of about 1, 5 or 10 cm$^3$. However, under certain circumstances, for example in the case where the implant material is not very porous or resorbable, it may be appropriate for even smaller implant sites. The actual volume of the implant may not be as important a selection factor as the dimension of a cross-sectional area. The cross-section is defined as the distance across which a remodeling must occur in order to integrate the implant with its host. The shorter that distance, the faster integration can be completed. Implants having a cross section in any direction of greater than 2–3 mm, and preferably greater than 1 cm, are suitable candidates for incorporation of access means of the invention.

In one embodiment, the implant may be prepared as an injectable paste. A liquid is added to a dry powder to form a paste of injectable consistency. The paste may be introduced into the implant site by syringe, preferably an 18 or 16 gauge syringe. In this case, access means are best introduced into the paste after the paste has been injected into the implant site. Access channels may be inserted by pressing the macro structures into the paste which has been applied to the implant site. Alternatively, a channel former may be introduced by sequential addition of malleable implant material and channel former. For example, a layer of the paste is formed, a layer of channel former in the form of a sheet or rods is then laid onto or pressed into the paste layer and a second layer of paste is applied. This layering may be carried out one or more times, to provide a stratified malleable implant having channel formers imbedded therein.

In some embodiments, it may be desirable to prepare the paste first and to mix the macro structures into the paste prior to implantation. The access channels may be introduced by finger massaging the structures in with the paste. Alternatively, in those instances where the access channel is in the form of a sheet or layer, the paste may be applied by brush or other suitable applicator onto the access layer to form a laminate structure. Implantation is best accomplished by bulk application, as the macro structure may not pass through instrumentation, e.g., a syringe, otherwise suitable for applying the paste.

In still other embodiments, the macro structures of the access means are introduced into a dry powder precursor to the paste. Subsequently, fluid is added to the powder to form the paste, which may then be applied to the site. The dry precursor powder mixture including access means may be applied directly to a host site. Hydration of the powders occurs in vivo upon contact of the powder with blood and other physiological liquids. Such an application method may be particularly desirable when implantation is accompanied by excessive bleeding. The hygroscopic nature of the dry powder then serves a dual purpose of providing a physical barrier to protect the wound site and to provide an implant material for tissue growth.

The invention may be accomplished as shown in the following examples, which are presented for the purpose of illustration only and which are not limiting of the invention, the full scope of which is set forth in the claims which follow.

This example illustrates the preparation of an apatitic calcium phosphate implant including access channels. The calcium phosphate implant material may be prepared as described in this example, or it may be obtained from commercially available sources, such as Alpha BSM (Etex Corporation), SRS (Norian Corporation) and Bone Source (Howmedica Leibinger, Inc.).

Dicalcium phosphate dihydrate (DCPD) was prepared at room temperature by the rapid addition of solution B (17.1 g $Ca(NO_3)_2(4H_2O$; 0.250 liters distilled water; pH 5.5–6) to a stirred solution A (10 g $H_9N_2O_4P$; 0.5 liters distilled water; pH 7.8). Immediately thereafter, the sample was filtered using filter paper (0.05 sq. m) with medium filter speed and a vacuum pressure of about 10-2 torr. The material formed a thin cake which was washed with about 2 liters of distilled water and then dried at room temperature for 24–72 hours.

Reactive amorphous calcium phosphate was prepared according to example 1. The washed material was then collected using a spatula and immersed into a liquid nitrogen in a 2.5 L container. Following freezing, the material was transferred into a vacuum chamber for 24 hours ($10^{-1}$–$10^2$ torr), until a fine and dry powder was obtained. The material was then heated for 80 minutes at 455° C. ((3° C.).

The reactive amorphous calcium phosphate material was physically dry-mixed with $CaHPO_4 2H_2O$ at 50:50 weight percent using a mortar and pestle for 3–5 minutes. Water (1 ml/g of mixed material) was then added to the powder mixture to yield a hydrated precursor of paste-like consistency. The amount of H2O added varied, depending on whether a thick or thin paste was desired. The paste material was then placed in a moist tissue environment where upon reaching body temperature (37° C.), it hardened into a solid mass. The hardening process could be delayed for several hours by placing it into a refrigerating temperature of 4° C.

The paste as described above is introduced into a host site. For example, a non-union bone, e.g., the tibia, of a host is exposed, and the site cleared of debris and otherwise prepared for implantation. The paste material above, prepared with a saline solution, is introduced into the break. Pressed powder rods of highly resorbable material, e.g., sugar, are inserted into the cement. Rods are about 1 cm in length and 1 mm in width. When complete, the soft tissues are then closed in layers.

What is claimed is:
1. An implant for implantation into an implant site of living tissue, comprising:
   a malleable implant material, capable of being deformed under pressure required to insert the malleable implant material into the implant site; and
   a non-particulate, bioresorbable solid element having a greater resorption rate in vivo than the implanted malleable implant material, or the element comprising a mechanically weak material susceptible to fracturing under force at the implant site resulting in channels or cracks, at least a portion of the element being contained in the interior of the malleable implant material, for providing macroscopic access into the interior of the implant to cells of the living tissue by the element more rapidly resorbing in vivo than the implanted malleable implant material, or the element fracturing under force at the implant site to produce channels or cracks.

2. The implant of claim 1, wherein the implant has at least one cross-sectional dimension of greater than 3 mm.

3. The implant of claim 1, wherein the implant has at least one cross-sectional dimension of greater than 1 cm.

4. The implant of claim 1, wherein the malleable implant material is comprised of a bioresorbable material and a physiologically acceptable fluid.

5. The implant of claim 1, wherein the malleable implant material is selected from the group consisting of calcium phosphates, collagens, and fibrins.

6. The implant of claim 1, wherein the malleable implant material is hardenable.

7. The implant of claim 1, wherein the malleable implant material comprises an osteoconductive material.

8. The implant of claim 5, wherein the calcium phosphate is selected from the group consisting of amorphous calcium phosphate, tricalcium phosphate, hydroxyapatite, calcium deficient hydroxyapatite, poorly crystalline hydroxyapatite (PCHA), dicalcium phosphate dihydrate (DCPD), tetracalcium phosphate, and dahlite ($Ca_5(PO_4,CO_3)_3F$).

9. The implant of claim 1, wherein the element is selected from the group consisting of rods, fibers, sheets, fibrous mats, star-shapes and jack-shapes.

10. The implant of claim 1, wherein the element has an outer diameter greater than that of cells of the living tissue.

11. The implant of claim 1, wherein the element is selected from the group consisting of poly(lactide), poly(lactide-co-glycolide), gelatins, collagen, alginate, tissue culture medium, calcium phosphates, calcium sulfate, sugars, carbohydrates, and salts.

12. The implant of claim 1, wherein the element is comprised of a material resorbable by dissolution, enzymatic action or cellular action to provide cellular access to the interior of the implant.

13. The implant of claim 1, wherein the element is comprised of a nutrient of a cell of the living tissue.

14. The implant of claim 1, wherein the element comprises a polymer capable of acting as a substrate for cell attachment.

15. The implant of claim 1, further comprising a material for promoting cell adhesion.

16. The implant of claim 1, wherein the element has a dimension greater than 0.5 mm.

17. The implant of claim 1, wherein the element has a dimension greater than 1 mm.

18. The implant of claim 1, wherein the element has a dimension greater than 5.0 mm.

19. The implant of claim 1, wherein the element is insertable into the malleable implant material at an implant site.

20. The implant of claim 1, wherein the implant is a multilaminar structure having layers of malleable implant material and element.

21. The implant of claim 1, wherein the element is heterogeneously distributed throughout the implant.

22. The implant of claim 1, further comprising additives capable of controlling the resorption rate of the implant material.

23. The implant of claim 22, wherein the additives are selected from the group consisting of bone morphogenic protein, OP-1 parathyroid hormone, parathyroid-hormone-related peptide, 1,25-dihydroxyvitamin D, interleukin-1, tumor necrosis factor, thyroid hormones, vitamin A, transforming growth factor/epidermal growth factor, fibroblast growth factor, heparin, bacterial endotoxin, thrombin, bradykinin, prostaglandin $E_2$, transforming growth factor β, lymphocyte inhibitory factor/differentiation inducing factor, calcitonin, interferon-γ, glucocortinoids, estrogens, and androgens.

24. The implant of claim 1, further comprising reinforcing additives.

25. An implant for implantation into an implant site of living tissue comprising:
   a biocompatible, hardened implant material; and
   a non-particulate, bioresorbable, solid element having a greater resorption rate in vivo than the hardened implant material, or the element comprising a mechanically weak material susceptible to fracturing under force at the implant site resulting in channels or cracks, at least a portion of the element being contained in the interior of the hardened implant material, for providing macroscopic access into the interior of the hardened implant material to cells of the living tissue by the element more rapidly resorbing in vivo than the hardened implant material, or the element fracturing under force at the implant site to produce channels or cracks.

26. The implant of claim 25, wherein the biocompatible, hardened implant material comprises an osteoconductive material.

27. The implant of claim 25, wherein the biocompatible, hardened implant material is selected from the group consisting of calcium phosphates, collagens, and fibrins.

28. The implant of claim 27, wherein the calcium phosphate is selected from the group consisting of amorphous calcium phosphate, tricalcium phosphate, hydroxyapatite, calcium deficient hydroxyapatite, poorly crystalline hydroxyapatite (PCHA), dicalcium phosphate dihydrate (DCPD), tetracalcium phosphate, and dahlite ($Ca_5(PO_4, CO_3)_3F$).

29. The implant of claim 25, wherein the element is selected from the group consisting of rods, fibers, sheets, fibrous mats, star-shapes and jack-shapes.

30. The implant of claim 25, wherein the element has an outer diameter greater than that of cells of the living tissue.

31. The implant of claim 25, wherein the element has a dimension greater than 0.5 mm.

32. The implant of claim 25, further comprising a material for promoting cell adhesion.

33. A kit for applying an implant into an implant site of living tissue comprising:
   a powder for use in preparing a paste implant material; and
   a non-particulate, bioresorbable solid element insertable into the paste implant material, said element having a greater resorption rate in vivo than the implanted paste implant material, or the element comprising a mechanically weak material susceptible to fracturing under force at the implant site resulting in channels or cracks, and said element providing macroscopic access into the interior of the implant to cells of the living tissue by the element more rapidly resorbing in vivo than the implanted paste implant material, or the element fracturing under force at the implant site to produce channels or cracks.

34. The kit of claim 33, further comprising a mixing pouch.

35. The kit of claim 33, further comprising a physiologically acceptable fluid.

36. The kit of claim 33, wherein the powder comprises a calcium phosphate.

37. A method of making an implant and implanting the implant into an implant site of a host, comprising:
   implanting a malleable implant material into an implant site of a host, wherein said malleable implant material is capable of being deformed under pressure required to insert the malleable implant material into the implant site; and,
   before or after implanting said malleable implant material, introducing a non-particulate, bioresorbable solid element into the malleable implant material for providing macroscopic access into the interior of the implant to cells of the host, wherein said macroscopic access results from said element more rapidly resorbing in vivo than the implanted malleable implant material, or the element comprising a mechanically weak material and fracturing under force at the implant site to produce channels or cracks.

38. The method of claim 37, wherein the implant has at least one cross-sectional dimension of greater than 3 mm.

39. The method of claim 37, wherein the implant has at least one cross-sectional dimension of greater than 1 cm.

40. The method of claim 37, wherein the malleable implant material is comprised of a bioresorbable material and a physiologically acceptable fluid.

41. The method of claim 37, wherein the malleable implant material is hardenable.

42. The method of claim 37, wherein the malleable implant material comprises an osteoconductive material.

43. The method of claim 42, wherein the osteoconductive material is selected from the group consisting of calcium phosphates, collagens, and fibrins.

44. The method of claim 43, wherein the calcium phosphate is selected from the group consisting of amorphous calcium phosphate, tricalcium phosphate, hydroxyapatite, calcium deficient hydroxyapatite, poorly crystalline hydroxyapatite (PCHA), dicalcium phosphate dihydrate (DCPD), tetracalcium phosphate, and dahlite ($Ca_5(PO_4, CO_3)_3F$).

45. The method of claim 37, wherein the element is selected from the group consisting of rods, fibers, sheets, fibrous mats, star-shapes and jack-shapes.

46. The method of claim 37, wherein the element has an outer diameter greater than that of cells of the living tissue.

47. The method of claim 37, wherein the element is selected from the group consisting of poly(lactide), poly (lactide-co-glycolide), gelatins, collagen, alginate, tissue culture medium, calcium phosphates, calcium sulfate, sugars, carbohydrates, and salts.

48. The method of claim 37, wherein the element is comprised of a material resorbable by dissolution, enzymatic action or cellular action to provide access to the interior of the implant.

49. The method of claim 37, wherein the element is comprised of a nutrient of a cell of the living tissue.

50. The method of claim 37, wherein the element comprises a polymer capable of acting as a substrate for cell attachment.

51. The method of claim 37, wherein the implant further comprises a material for promoting cell adhesion.

52. The method of claim 37, wherein the element has a dimension greater than 0.5 mm.

53. The method of claim 37, wherein the element has a dimension greater than 1 mm.

54. The method of claim 37, wherein the element has a dimension greater than 5.0 mm.

55. The method of claim 37, wherein the element is insertable into the malleable implant material at an implant site.

56. The method of claim 37, wherein the implant is a multilaminar structure having layers of malleable implant material and element.

57. The method of claim 37, wherein the element is heterogeneously distributed throughout the implant.

58. The method of claim 37, wherein the implant further comprises additives capable of controlling the resorption rate of the implant material.

59. The method of claim 37, wherein the implant further comprises reinforcing additives.

60. A method of making an implant and implanting the implant into an implant site of a host, comprising:

providing a paste implant material capable of hardening;

before said paste implant material hardens, introducing a non-particulate, bioresorbable, solid element into the paste implant material for providing macroscopic access into the interior of the hardened implant material to cells of the host, allowing said paste implant material to harden; and implanting said hardened implant material into an implant site of a host, wherein said macroscopic access results from said element more rapidly resorbing in vivo than the hardened implant material, or the element containing a mechanically weak material and fracturing under force at the implant site to produce channels or cracks.

61. The method of claim 60, wherein the hardened implant material comprises an osteoconductive material.

62. The method of claim 60, wherein the hardened implant material is selected from the group consisting of calcium phosphates, collagens, and fibrins.

63. The method of claim 62, wherein the calcium phosphate is selected from the group consisting of amorphous calcium phosphate, tricalcium phosphate, hydroxyapatite, calcium deficient hydroxyapatite, poorly crystalline hydroxyapatite (PCHA), dicalcium phosphate dihydrate (DCPD), tetracalcium phosphate, and dahlite ($Ca_5(PO_4, CO_3)_3F$).

64. The method of claim 60, wherein the element is selected from the group consisting of rods, fibers, sheets, fibrous mats, star-shapes and jack-shapes.

65. The method of claim 60, wherein the element has an outer diameter greater than that of cells of the living tissue.

66. The method of claim 60, wherein the element has a dimension greater than 0.5 mm.

67. The method of claim 60, wherein the hardened implant material further comprises a material for promoting cell adhesion.

* * * * *